(12) United States Patent
Hammer

(10) Patent No.: US 8,205,845 B2
(45) Date of Patent: Jun. 26, 2012

(54) HOLDING ARRANGEMENT HAVING A WEIGHT BALANCE

(75) Inventor: Hermann Hammer, Hemmental (CH)

(73) Assignee: Carl Zeiss Meditec AG, Jena (DE)

( * ) Notice: Subject to any disclaimer, the term of this patent is extended or adjusted under 35 U.S.C. 154(b) by 548 days.

(21) Appl. No.: 12/149,621

(22) Filed: May 6, 2008

(65) Prior Publication Data

US 2008/0237413 A1   Oct. 2, 2008

Related U.S. Application Data

(63) Continuation of application No. PCT/EP2006/010777, filed on Nov. 10, 2006.

(51) Int. Cl.
*E04G 3/00* (2006.01)
*G02B 21/00* (2006.01)

(52) U.S. Cl. ........... 248/276.1; 248/280.11; 248/281.11; 248/285.1; 359/384

(58) Field of Classification Search ............... 248/277.1, 248/278.1, 123.11, 291.1, 162.1, 585, 281.11, 248/280.11, 324, 648, 123.2, 276.1

See application file for complete search history.

(56) References Cited

U.S. PATENT DOCUMENTS

| | | | |
|---|---|---|---|
| 3,973,748 A | | 8/1976 | Nagasaka |
| 4,277,044 A | | 7/1981 | Hamilton |
| 4,344,595 A | * | 8/1982 | Heller et al. ................. 248/542 |
| 4,768,762 A | | 9/1988 | Lund |
| 5,173,802 A | * | 12/1992 | Heller ............................ 359/384 |
| 5,213,293 A | | 5/1993 | Muentener et al. |
| 5,492,296 A | | 2/1996 | Biber |
| 5,812,301 A | * | 9/1998 | Nakamura .................... 359/384 |
| 6,105,909 A | * | 8/2000 | Wirth et al. ................ 248/123.2 |
| 6,514,239 B2 | * | 2/2003 | Shimmura et al. ................ 606/1 |
| 6,523,796 B2 | | 2/2003 | Abramowsky et al. |
| 6,730,247 B2 | | 5/2004 | De Winter et al. |
| 6,732,988 B2 | * | 5/2004 | Ihalainen et al. .......... 248/276.1 |
| 6,763,286 B2 | * | 7/2004 | Metelski ....................... 700/279 |
| 6,998,085 B2 | | 2/2006 | De Winter et al. |
| 2004/0245419 A1 | | 12/2004 | Sweere et al. |

FOREIGN PATENT DOCUMENTS

| | | |
|---|---|---|
| DE | 195 41 759 | 5/1997 |
| EP | 0 323 891 | 7/1989 |
| EP | 323891 A2 * | 7/1989 |
| EP | 0 628 290 | 12/1994 |
| FR | 2 605 757 | 4/1988 |
| WO | WO 85/02524 | 6/1985 |

OTHER PUBLICATIONS

English translation of the office action of the German Patent Office dated May 18, 2006 in the parallel German application. English translation of the office action of the European Patent Office dated Nov. 10, 2008 in the parallel European application.
English translation of the office action of the Japanese Patent Office dated Jan. 4, 2012 in the parallel Japanese application.

\* cited by examiner

*Primary Examiner* — Amy Sterling
*Assistant Examiner* — Erin W Smith
(74) *Attorney, Agent, or Firm* — Walter Ottesen

(57) ABSTRACT

A holding arrangement is suitable especially for medical-optical equipment (108). The holding arrangement includes a carrier arm (101) for accommodating a load. The carrier arm (101) is pivotally mounted on a holder (102) with the aid of a first rotational joint (103). The holding arrangement further includes a linear spring arrangement (120) for generating a longitudinal force which acts upon the carrier arm (101) in order to compensate a load torque arising in the first rotational joint (103) of the carrier arm (101). The linear spring arrangement (120) for generating a longitudinal force is pivotally mounted on the holder (102) and applies a force on a curved carrier (119) which is operatively connected to the carrier arm (101).

38 Claims, 6 Drawing Sheets

HOLDING ARRANGEMENT HAVING A WEIGHT BALANCE

CROSS REFERENCE TO RELATED APPLICATIONS

This application is a continuation application of international patent application no. PCT/EP 2006/010777, filed Nov. 10, 2006, designating the United States of America and claiming priority from German patent application no. 10 2005 054 010.4, filed Nov. 10, 2005, and the entire content of both applications is incorporated herein by reference.

FIELD OF THE INVENTION

The invention relates to a holding arrangement and especially a holding arrangement for a medical-optical instrument. The holding arrangement has a carrier arm for accommodating a load and the carrier arm is pivotally journalled with a first rotational joint relative to a holder. The carrier arm includes means for generating a longitudinal force which acts on the carrier arm to balance a load torque occurring at the first rotational joint of the carrier arm.

BACKGROUND OF THE INVENTION

A holding arrangement of the kind referred to above is disclosed in U.S. Pat. No. 6,523,796. There, a surgical microscope stand is described having a first link and a second link which are articulately connected at a common pivot base. The first and second links form a parallel link construction in that they are connected at their front ends by a front link. A surgical microscope is mounted on this front link. A load torque occurs at the pivot base and is caused by a load taken up on the parallel link construction. To compensate this load torque, a force storage element is provided in the parallel link construction and this storage element is configured as a linear spring. This force storage element is pivotally connected to one of the carrier links of the parallel link construction and applies a tension or pressure force to the pivot base in order to hold the surgical microscope, which is accommodated on the parallel link construction, in a floating state.

U.S. Pat. No. 5,213,293 discloses a carrier arrangement for medical-optical equipment wherein a force storage element is provided for generating a linear force with this force storage element being in a frame arm of a surgical microscope stand. The force storage element is supported on the pivot base of the frame arm in a guide in order to compensate a changing force of the force storage element which is dependent upon the stroke.

U.S. Pat. No. 5,492,296 discloses a surgical microscope stand wherein a surgical microscope is accommodated on a stand and is movably accommodated via rotational joints on a pivot axis and a tilt axis. Torsion springs are assigned to the rotational joints for balancing a load torque caused in the rotational axis and tilt axis by the surgical microscope. The pretensioning of the torsion springs can be adjusted.

European patent publication 0 628 290 discloses a surgical microscope stand wherein a surgical microscope is carried by a parallel link construction which is supported on a stand console with a pivotal support point so as to be pivotally movable. Balancing masses are provided on the surgical microscope stand to balance a load torque occurring at the parallel link construction. The balancing masses compensate the weight of the surgical microscope accommodated on the parallel link construction.

SUMMARY OF THE INVENTION

It is an object of the invention to provide a holding arrangement having a low inherent weight which makes possible a force-free guidance of an accommodated load when moving the carrier arm in a rotational joint on the holder.

The above object is achieved with the holding arrangement of the kind referred to above wherein the means for generating a longitudinal force is pivotally journalled on the holder and applies a force to a curved carrier which is operatively connected to the carrier arm. In this way, the weight of the means for generating the longitudinal force does not load the carrier arm. This ensures that the means for generating the longitudinal force to compensate for a load torque in the rotational joints of the carrier arm need not also compensate its inherent weight.

According to another feature of the invention, the carrier arm is pivotally connected to the holder. In this way, it is possible to provide a rigid connection of curved carrier and carrier arm in order to balance a load torque on the carrier arm with the means for generating a longitudinal force.

According to another feature of the invention, the means for generating a longitudinal force includes one spring element or several spring elements. A corresponding spring element can, for example, be configured as a linear spring, that is, as a spring element wherein a generated spring force is proportional to a deflection of the spring element which deforms the spring element. It is, however, basically also possible to provide one or several spring elements which have a non-linear relationship between a deflection, which deforms the spring element, and a spring force caused by the deflection. An especially reliable holding arrangement is provided with the use of several spring elements. This holding arrangement requires no maintenance and can be especially reliably moved even when there is a fracture of a spring.

According to another feature of the invention, the means for generating a longitudinal force acts on a bearing element which rolls off on the guide when the carrier arm moves on the holder. In this way, it is possible to minimize friction forces.

According to another feature of the invention, the point, at which the means for generating a longitudinal force acts, can be shifted on the holder in at least one direction, preferably, in two directions. In this way, it is possible to adjust the holding arrangement for weight balancing when there is a change of the load accommodated thereon.

According to another feature of the invention, a gear assembly is provided to adjust the point of action of the means for generating a longitudinal force on the holder. In this way, the holding arrangement can be precisely adjusted for weight balance when a load weight changes.

According to another feature of the invention, a motor is provided to adjust the point of action of the means for generating a longitudinal force on the holder. In this way, the conditions precedent for the automatic adjustment of the balanced weight state in the holding arrangement are achieved.

In a further feature of the invention, the holder with a longitudinal guide is accommodated in a base unit. In this way, a free movement of a load, which is accommodated on the carrier arm, is possible.

According to another feature of the invention, the carrier arm is connected on the holder via a rotational joint to a second carrier arm which carries the load. A first means and a second means for generating a longitudinal force are pivotally journalled on the holder and the first means applies a force to a guide which is operatively connected to the carrier arm and the second means for generating a longitudinal force acts on a guide which is operatively connected to the second carrier arm. In this way, it is possible to move, with the holding arrangement, without force a load which is accommodated on a multi-link carrier arm.

According to another feature of the invention, a second rotational joint is provided on the holding arrangement which makes it possible to pivot the carrier arm about an axis different from the axis of the first rotational joint. In this way, a load, which is accommodated on the carrier arm, can be positioned at any desired location in space.

According to a further feature of the invention, the second rotational joint connects the base unit to a stand console. In this way, a modular assembly of the holding arrangement is provided.

According to another feature of the invention, a front link is provided in the holding arrangement which is pivotally connected to a third rotational joint at a front end of the carrier arm in order to hold a load on the carrier arm.

According to another feature of the invention, an operative connection of front link and holder ensures an alignment of the front link which remains the same independently of the position of the carrier arm. In this way, it is possible to move a load, which is carried on the front link, with respect to the front link, that is, it is possible to shift the center of gravity without the load torque changing in the first rotational joint for a given position of the carrier arm.

According to another feature of the invention, the operative connection is configured as a tension means, especially, as a cable or as a parallel link construction.

According to another feature of the invention, a receptacle for an additional weight is arranged in the carrier arm. In this way, it is possible to compensate a change of a load accommodated on the carrier arm with an additional weight so that the holding arrangement can be moved free of force without acting on the means for generating a longitudinal force.

In a further embodiment of the invention, the additional weight can be shifted on the carrier arm in order to change a load torque occurring in the first rotational joint of the carrier arm. In this way, the holding arrangement can be adapted especially simply to different load weights which act on the carrier arm.

According to another feature of the invention, the curved carrier is configured in the form of a clothes hook. In this way, it is possible to introduce the force, which is generated by means for generating a longitudinal force, directly into the curved carrier via a roller guided on the curved carrier.

The curved carrier can, however, also have a kidney shape. With this curved carrier form, a large freedom of movement of the holding arrangement is achieved.

The holding arrangement can be especially configured as a surgical microscope ceiling stand, a surgical microscope wall stand or as a surgical microscope floor stand.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
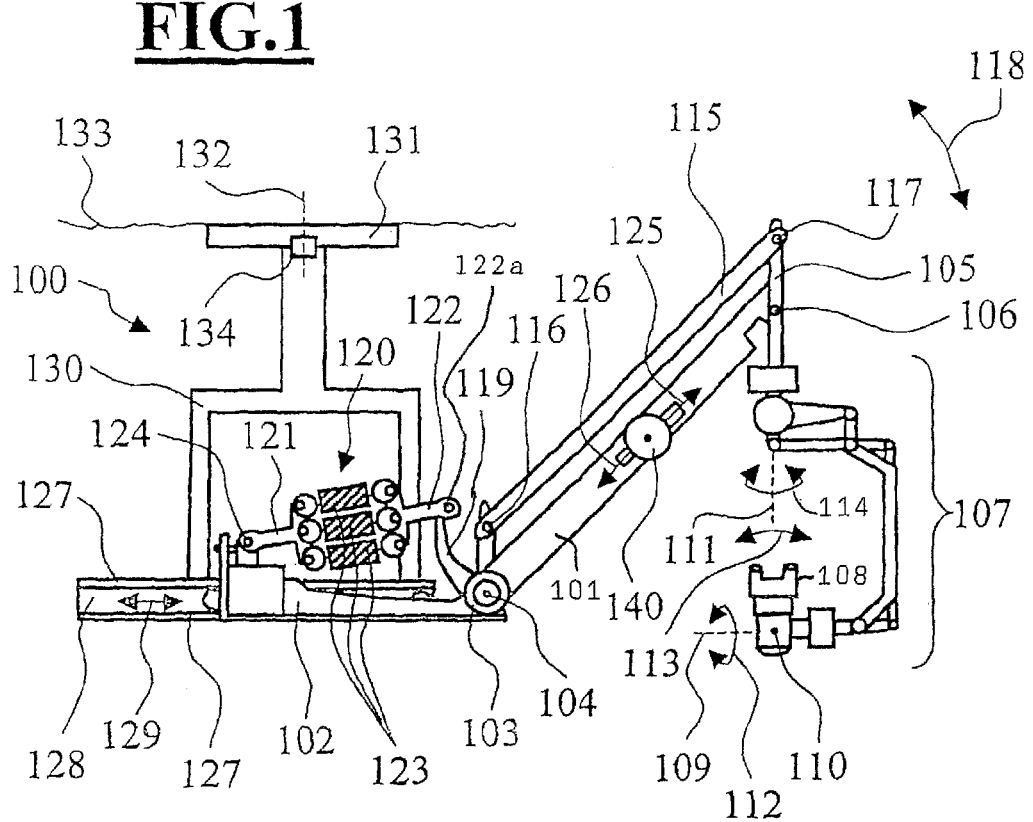
FIG. 1 shows a first embodiment of a holding arrangement configured as a surgical microscope ceiling stand.

In FIG. 1, a surgical microscope ceiling stand 100 is shown which includes a carrier arm 101 pivotally journalled about an axis 104 with a rotational joint 103 on a holder 102. A front link 105 is held in a rotational joint 106 on the carrier arm 101. The front link 105 carries a medical-optical equipment unit 107 having a surgical microscope 108. The surgical microscope 108 can be moved about axes (109, 110, 111) in the directions indicated by arrows 112 to 114. A link 115 is arranged parallelly to the carrier arm 101 and is assigned to the front link 105. This link 115 is supported on the holder 102 with the rotational joint 116 and is connected to the front link 105 via a rotational joint 117. This ensures that the front link 105 is always vertically aligned in the same manner with a pivot movement of the carrier arm 101 about the axis 104 in the direction indicated by the double arrow 118. It is noted that, in lieu of a link 115, it is also possible to couple the front link 105 to the holder 102 via a cable mechanism or a rack and pinion gear assembly in order to ensure alignment of the front link 105 which remains the same when shifting the surgical microscope ceiling stand 100.

A hook-shaped curved carrier 119 is rigidly connected to the carrier arm 101. A linear spring arrangement 120 acts on this hook-shaped curved carrier 119 as a means for generating a longitudinal force. The linear spring arrangement 120 has a first spring holding body 121 and a second spring holding body 122 between which the spring blocks 123 are held. The first spring holding body 121 is accommodated pivotally on the holder 102 via a rotational joint 124. The second spring holding body 122 carries a roller journalled in a bearing 122a. The roller rolls off on the curved carrier 119 when there is a movement of the carrier arm 101 in the direction indicated by the double arrow 118. The bearing for the roller can, for example, be a slide bearing, ball bearing or needle bearing.

The curved carrier 119 is so configured that the load torque, which is caused in the axis 104 of the rotational joint 103 by the surgical microscope 108 accommodated on the carrier arm, is precisely compensated by the load torque of the linear spring arrangement 120 which applies a linear force to the curved carrier 119.

To ensure that the torque developing in the axis 104 can be exactly compensated when there is a change of a load mass of the surgical microscope, a displaceable additional weight 140 is provided on the carrier arm 101 which is movable in the direction of the arrows 125 and 126 along the carrier arm 101.

The holder 102 is accommodated in a sled-like longitudinal or linear guide 127 on a base unit 128. In this linear guide 127, the carrier arm 101 can be moved with the holder 102 in the direction indicated by the double arrow 129. The base unit 128 is held on a mounting unit 130 which can be rotated about a rotational axis 132 on a stand console 131 and is mounted on the ceiling 133 of an operating room.

Figure 2:
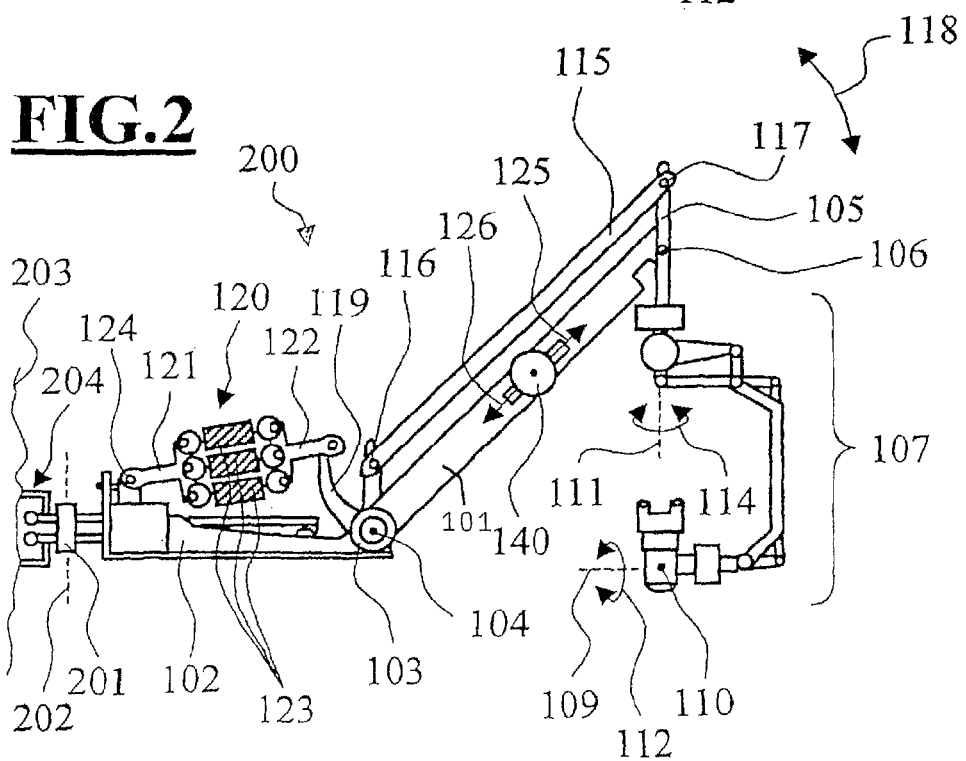
FIG. 2 is a schematic of a second holding arrangement configured as a surgical microscope wall stand.

FIG. 2 shows a holding arrangement configured as a surgical microscope wall stand 200. Insofar as the component assemblies of the holding arrangement correspond to those of the surgical microscope ceiling stand of FIG. 1, they have the same reference numerals here. In the surgical microscope wall stand, the holder 102 is pivotally connected to a rotational joint 201 having a rotational axis 202. The rotational joint 201, in turn, is held in a linear guide 204 arranged on a wall 203 of the operating room and can so be moved horizontally to the wall of the operating room.

Figure 3:
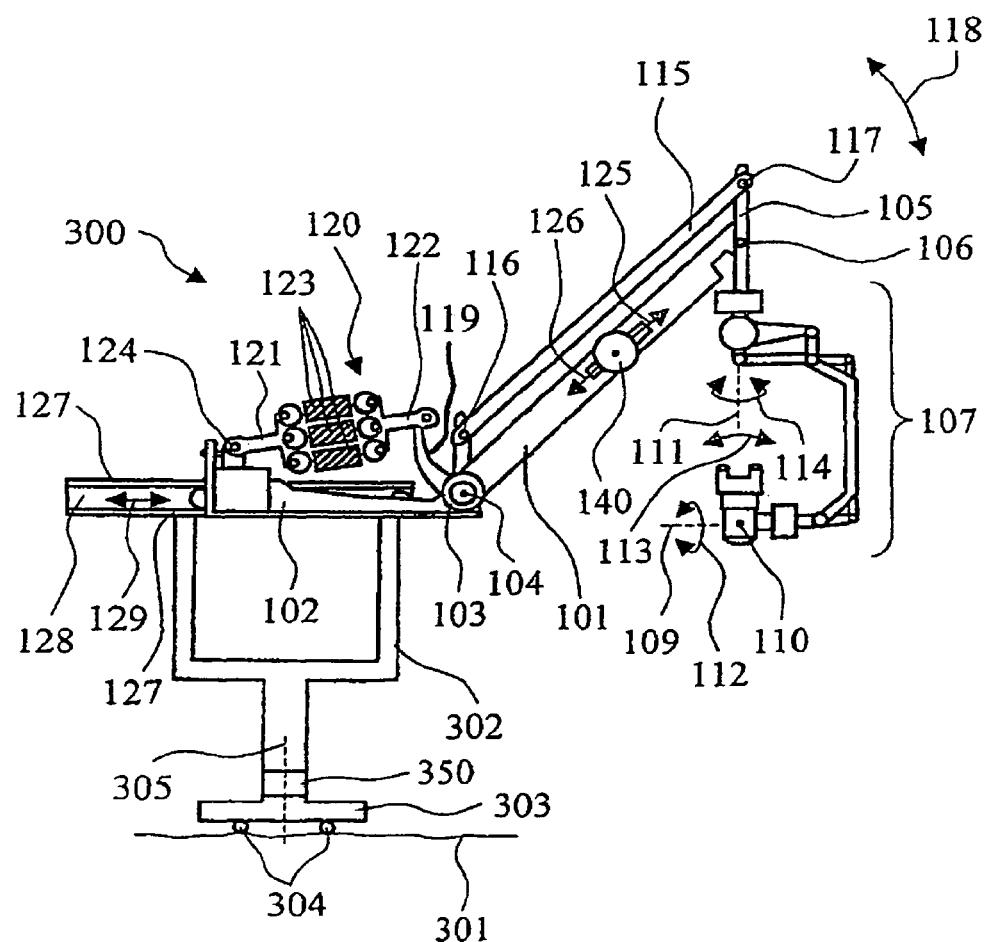
FIG. 3 is a schematic of a third holding arrangement configured as a surgical microscope floor stand.

FIG. 3 shows a holding arrangement 300 configured as a surgical microscope ceiling stand. The component assemblies of the holding arrangement have the same reference numerals insofar as they correspond to those component assemblies of the surgical microscope ceiling stand of FIG. 1. The holding arrangement 300 is different from the surgical microscope ceiling stand of FIG. 1 in that the base unit 128 is mounted with its linear guide 127 on a mounting unit 302 mounted on the floor 301 of an operating room. The mounting unit 302 is mounted on a console 303 having traveling rollers 304. The console 303 includes a rotational joint 350 which permits the mounting unit 302 to rotate about a vertical axis 305.

Figure 4:
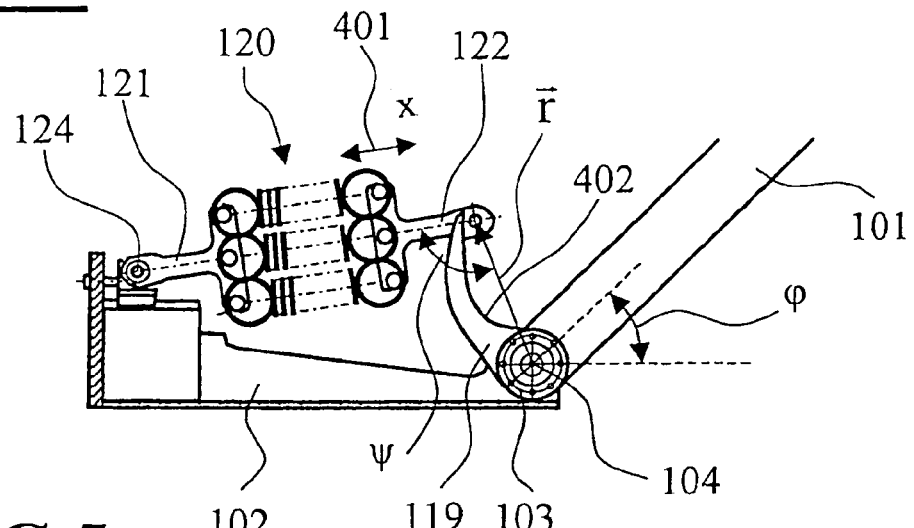
FIGS. 4 to 6 show an assembly group for different positions of the carrier arm with this assembly group being identical for the embodiments of FIGS. 1, 2 and 3.
Figure 5:
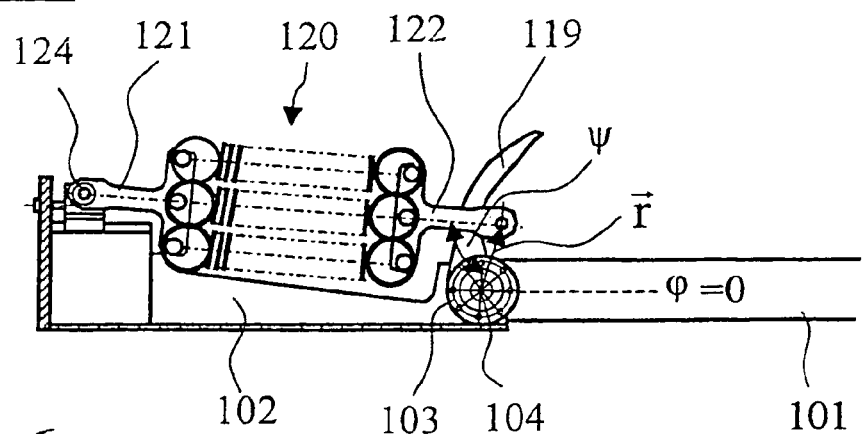
Figure 6:
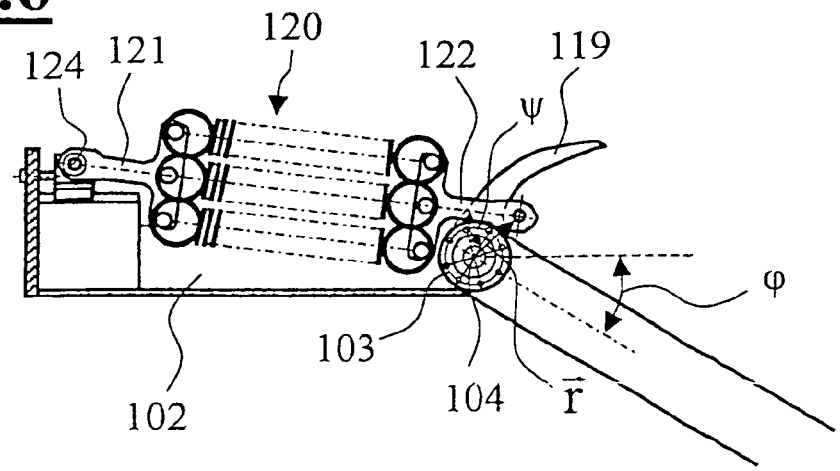

FIGS. 4, 5 and 6 show a detail of the holding arrangements described with respect to FIGS. 1 to 3 in order to explain the principle of the torque balance in the axis 104 of the rotational joint 103 for the carrier arm 101. The component assemblies of the holding arrangement section shown have reference numerals which are used to describe the holding arrangement of FIG. 1, 2 or 3.

In the holding arrangement, the linear spring arrangement 120 functions as an elastically deformable energy store whose expansion can be changed in the direction indicated by arrow 401. Corresponding to its expansion, a linear force is applied to the surface of the curved carrier 119 by the linear spring arrangement 120. This linear force is in the form of a spring force $\vec{F}_{spring}$. The spring force $\vec{F}_{spring}$ has the magnitude $|\vec{F}_{spring}|=Kx$ wherein K is a spring constant and x corresponds to the deflection of the spring from its rest state.

Referring to FIG. 4 wherein angles and forces are shown which occur in the holding arrangement, the form of the curved carrier 119 is determined by the following system of equations:

$$gML \cos \phi = |\vec{F}_{spring} \times \vec{r}| = k\{x-c\}r \sin \psi; \text{ torque balance} \quad (1)$$

$$\frac{1}{2}Kx^2 = ML\sin\varphi; \text{ conservation of energy} \quad (2)$$

$$\vec{F}_{spring} \cdot \frac{\delta \vec{r}}{\delta \varphi}\delta\varphi = 0; \text{ neutral equilibrium} \quad (3)$$

wherein:
g: acceleration due to gravity;
M: mass of the load accommodated on the carrier arm 101;
L: effective length of the carrier arm 101;
φ: angular position of the carrier arm;
$\vec{F}_{spring}$: spring force which is generated by the linear spring arrangement 120;
$\vec{r}$: location whereat the spring force acts on the hook-shaped guide element 119 functioning as a lever unit;
K: spring constant;
x: deflection of the energy store;
c: constant;
ψ: angle between spring force and the position vector of its application on the hook-shaped guide element 119.

Equation (1) expresses that, for balance, the torque, which is generated by means of the energy store in the form of the linear spring arrangement 120, is equal to the torque which the load on the carrier arm generates.

Equation (2) expresses the principle of energy conservation, that is, the sum of the potential energy of the linear spring arrangement 120 and the mass M, which is accommodated on the carrier arm 101, is unchangeable.

Equation (3) describes that the force of the linear spring arrangement 120 always acts perpendicularly on the surface 402 of the hook-shaped curved carrier 119. Equation (3) expresses that the linear spring arrangement 120 generates no forces which run tangential to the surface 402 of the curved carrier 119 and no forces that tend to move the curved carrier 119 with the carrier arm 101 in the rotational joint 103. In this way, the arrangement is in a rest state for each possible position of the linear spring arrangement. Equation (3) therefore means that the stand is in a neutral state of equilibrium for each possible position of the carrier arm 101.

The equations (1) to (3) correspond to the independent equation system of three implicit functions with respect to the four variables x, r, φ, ψ:

$$F_1(x,r,\phi,\psi)=0, F_2(x,r,\phi,\psi)=0, F_3(x,r,\phi,\psi)=0$$

In this way, the form of the hook-shaped curved carrier 119 is clearly determined. For a pregiven angle φ, the variables x, r and ψ are determined by this equation system.

Figure 7:
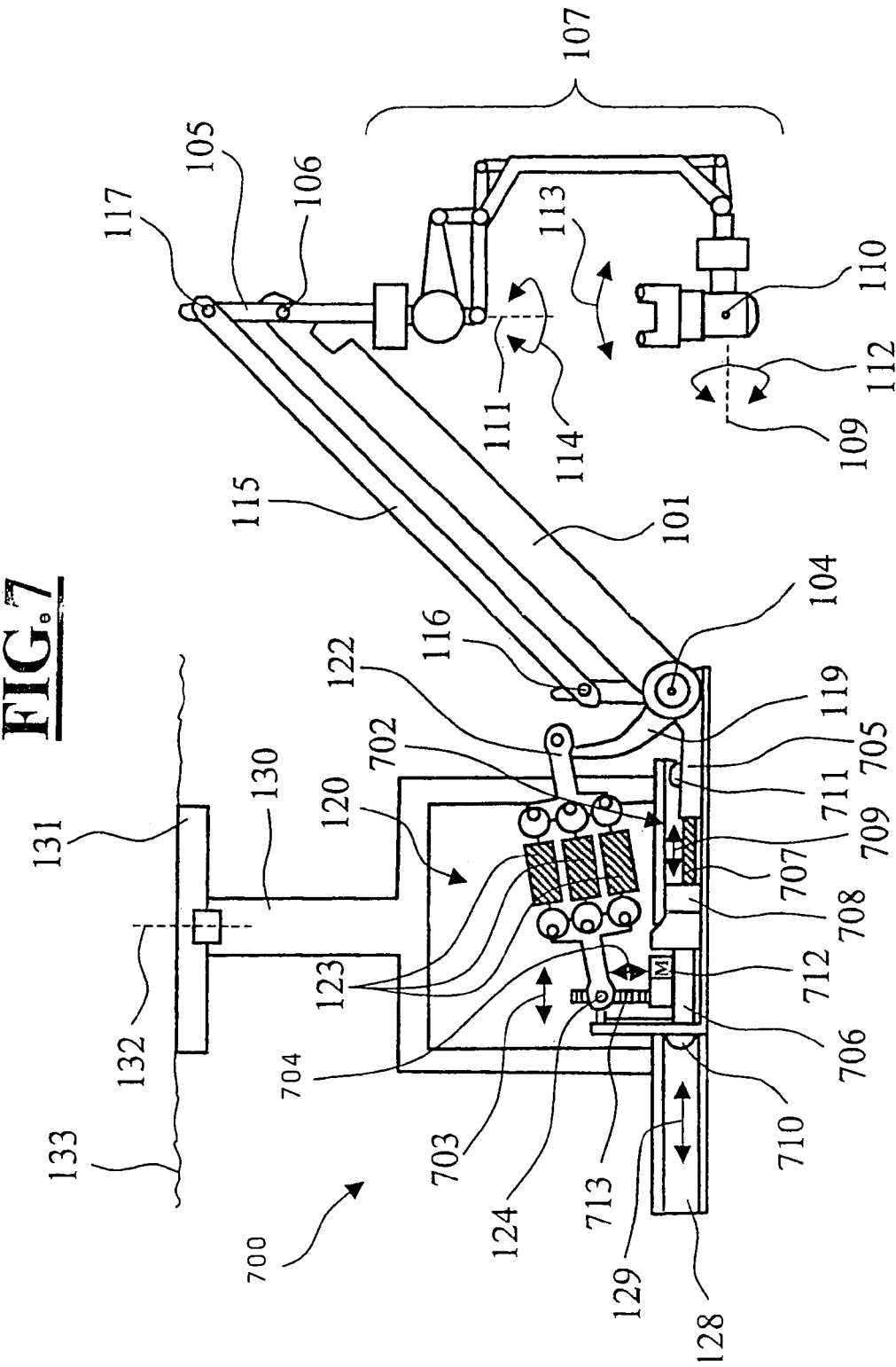
FIG. 7 shows a fourth embodiment of the holding arrangement in the form of a surgical microscope ceiling stand which is modified in comparison to the embodiment of FIG. 1.

FIG. 7 shows a surgical microscope ceiling stand 700 whose configuration corresponds basically to that of the surgical microscope ceiling stand 100 of FIG. 1. Insofar as the component assemblies of the stand in FIG. 7 correspond to those in FIG. 1, they have the same reference numerals.

What is different than in the surgical microscope ceiling stand 100 of FIG. 1 is, however, that in the surgical microscope ceiling stand 700, a holder 702 is provided which is linearly guided with rollers 710 and 711 on a base unit 128. In this holder, the rotational joint 124 can be displaced in the direction of the double arrows 703 and 704 with reference to the axis 104. For this purpose, the holder 702 includes a section 705 on which the rotational joint 104 is provided. Furthermore, the holder 702 has a section 706 which carries the rotational joint 124. The section 705 is connected via a threaded spindle 707 to the section 706. A gear unit having motor 708 is assigned to the threaded spindle 707. The section 705 of the holder 702 can be displaced relative to the section 706 of the holder 702 in correspondence to the double arrow 709 via a corresponding driving of the motor. The rotational joint 124 is then moved in the direction of the double arrow 703.

A further gear unit having motor 712 is mounted on section 706 of the holder. This additional gear unit functions to drive a threaded spindle 713. This threaded spindle 713 acts on the rotational joint 124. The rotational joint 124 is displaced in the direction of the double arrow 704 when moving the threaded spindle 713.

With a suitable driving of the gear unit with motor 708 and the gear unit with motor 712, it is possible to adjust a pretensioning of the linear spring unit 120 and to select the position of the points of application for the thereby generated spring force in the rotational joint 124 and on the curved carrier 119 so that the carrier arm 101 with the surgical microscope 108 accommodated thereon is held in balance in a pregiven position even when the mass of the surgical microscope accommodated on the carrier arm 101 changes.

No additional displaceable balance weight needs to be provided on the carrier arm 101 which is different from the ceiling stand 100 of FIG. 1 in order to ensure a force-free movement of the surgical microscope accommodated on the carrier arm 101 of the surgical microscope stand 700 when its mass is changed by connecting or removing peripheral apparatus.

Figure 8:
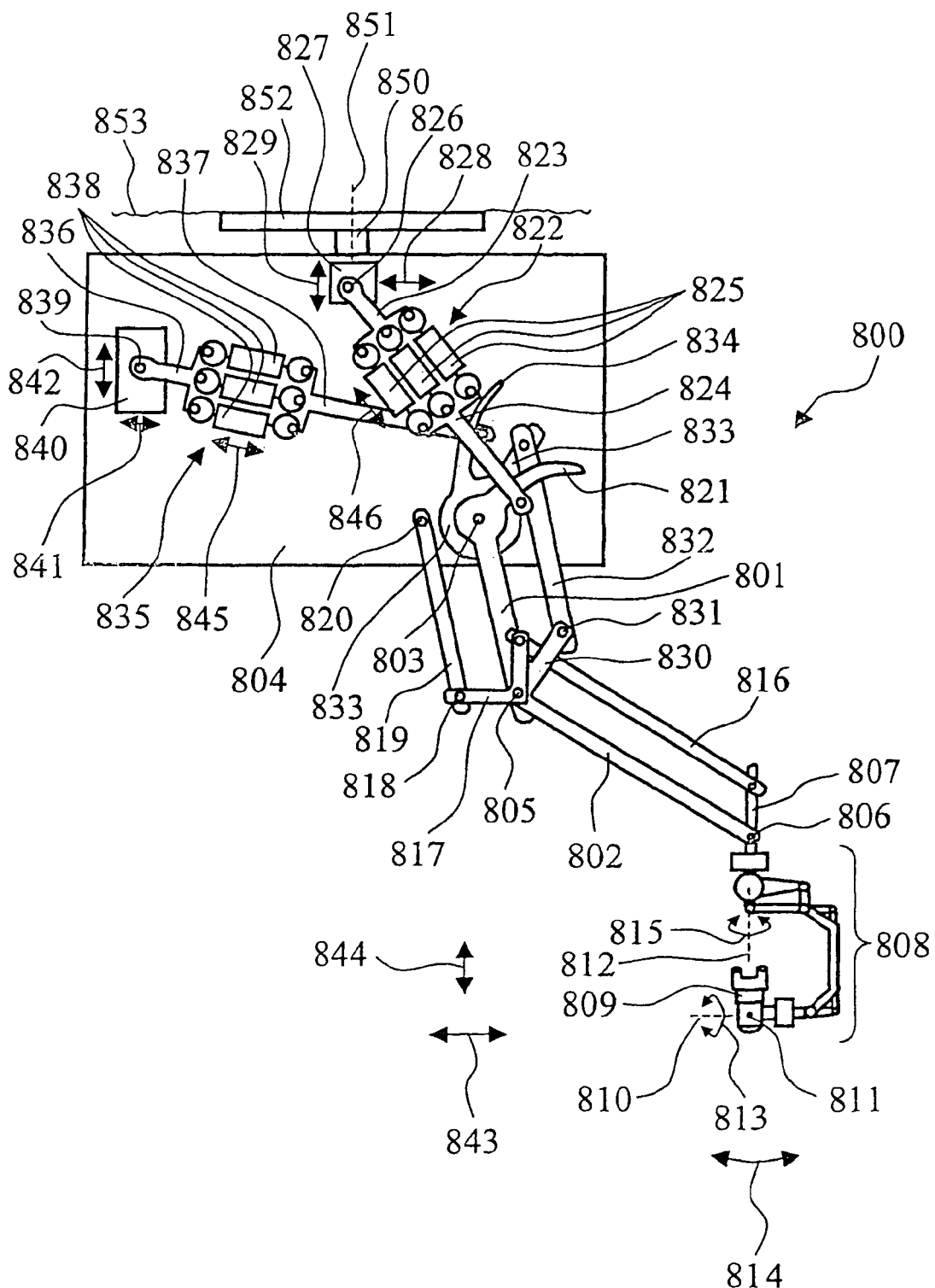
FIG. 8 is a schematic of a fifth embodiment of a holding arrangement in the form of a surgical microscope ceiling stand; and, FIG. 9 is a schematic of a sixth embodiment of a holding arrangement in the form of a surgical microscope ceiling stand.

FIG. 8 shows a surgical microscope ceiling stand 800 wherein a first carrier arm 801 and a second carrier arm 802 are provided. The first carrier arm 801 is held pivotally movable on a holder 804 in a rotational joint 803. The second carrier arm 802 is pivotally connected to the first carrier arm 801 in a rotational joint 805. The carrier arm 802 holds a vertical front link 807 with a medical-optical equipment unit 808 in a front end with a rotational joint 806. The equipment unit 808 includes a surgical microscope 809. The surgical microscope can be moved about axes (810, 811, 812) in the directions indicated by arrows (813, 814, 815) in the manner of the surgical microscope 108 of FIG. 1.

A link 816, which is arranged parallel to the second carrier arm 802, is assigned to the front link 807. This link 816 acts on a crank element 817 at the rotational joint 805. A link 819 is pivotally connected to this crank element 817 in a rotational joint 818. This link 819 is held on the holder 804 in a rotational joint 820.

A first hook-shaped curved carrier 821 is rigidly connected to the first carrier arm 801. A first linear spring arrangement 822 acts on the hook-shaped curved carrier 821 as means for generating a longitudinal force. As in the linear spring arrangement 120 of FIG. 1, the linear spring arrangement 822 has a first spring holder body 823 and a second spring holder body 824. Spring blocks 825 are held between the first and second spring holder bodies (823, 824). The spring holder body 823 is pivotally journalled on the holder 804 via a rotational joint 826. An adjusting unit is provided on the holder 804 and this adjusting unit permits the rotational joint 826 to be shifted on the holder 804 in the directions indicated by double arrows 828 and 829.

The second carrier arm 802 is rigidly connected to an angle piece 830 in the region of the rotational joint 805. A link 832 is pivotally connected to the angle piece 830 in a rotational joint 831. The link 832 acts on a crank unit 833 journalled on the holder 804 in the axis 803 of the rotational joint. The crank unit 833 includes a second curved carrier 834 which is configured to be hook-shaped like the curved carrier 821. A second linear spring arrangement 835 acts on this curved carrier 834. In the same manner as the linear spring arrangement 822, the linear spring arrangement 835 has a first spring holder body 836 and a second spring holder body 837. The spring blocks 838 are held between the first and second spring holder bodies (836, 837). The spring holder body 836 is pivotally journalled on the holder 804 with a rotational joint 839. An adjusting unit 840 is provided on the holder 804. With the adjusting unit 840, the rotational joint 839 can be shifted on the holder 804 in the directions indicated by the double arrows 841 and 842.

The holder 804 is held on a mounting unit 852 in a rotational joint 850 having a rotational axis 851. The mounting unit 852 is mounted on the ceiling 853 of an operating room (not shown).

The first linear spring arrangement 822 is so adjusted that it compensates a load torque caused by a load, which is taken up by the second carrier arm 802, in the axis of the rotational joint 803. The load taken up in the second carrier arm 802 is in the form of a medical-optical equipment unit 808.

The second linear spring arrangement 835 compensates a torque which is transmitted into the axis 803 of the rotational joint by the link 832. This torque is caused by the medical-optical-equipment unit 808 in the axis 805 of the rotational joint. It is noted that, basically, a transmission of the torque in the axis 805 of the rotational joint into the axis 803 of the rotational joint can also take place by a suitable other gear mechanism, for example, in the form of a pulley assembly or a toothed rack coupling.

With a shift of the medical-optical equipment 808 in the directions indicated by double arrows 843 and 844, the linear spring arrangements 822 and 835 are relaxed or expanded in the direction of the double arrows 845 and 846.

The adjusting units 827 and 840 for the rotational joints 826 and 839 of the linear spring arrangements 822 and 835 make it possible to adjust the surgical microscope stand 800 for weight balance so that the medical-optical equipment accommodated thereon can be moved free of force in the direction of double arrows 845 and 846.

Figure 9:
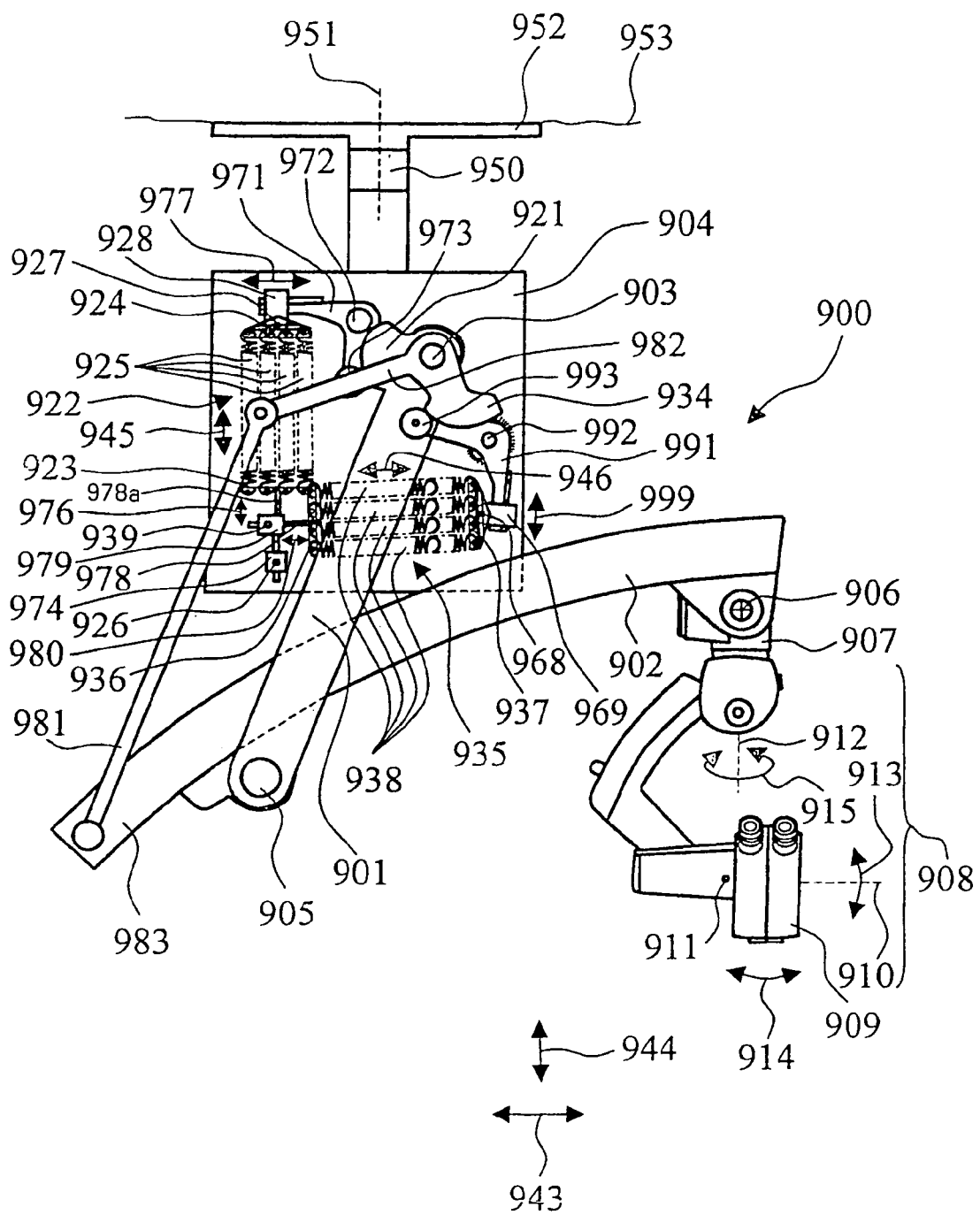

As a sixth embodiment of a holding arrangement, FIG. 9 shows a surgical-microscope ceiling stand 900 which, in turn, has a first carrier arm 901 and a second carrier arm 902. The first carrier arm 901 is pivotally movably held on a holder 904 in a rotational joint 903. The second carrier arm 902 is pivotally connected to a rotational joint 905 on the first carrier arm 901. In a front end, the carrier arm 902, holds with a rotational joint 906, a vertical front link 907 with a medical-optical equipment unit 908. The equipment unit 908 includes a surgical microscope 909. The surgical microscope can be moved about axes (910, 911, 912) in the directions indicated by arrows (913, 914, 915) in the same manner as the surgical microscope 108 of FIG. 1.

A first kidney-shaped curved carrier 921 is rigidly connected to the first carrier arm 901. A first linear spring arrangement 922 acts on the kidney-shaped curved carrier 921 as a means for generating a longitudinal force. The first linear spring arrangement 922 acts by means of a roller unit 973 via a lever element 971 which is journalled with a rotational joint 972 on the holder 904. As in the linear spring arrangement 120 of FIG. 1, the linear spring arrangement 922 has a first spring holder body 923 and a second spring holder body 924 between which the spring blocks 925 are held.

A spindle 978a and a spindle guide 974 having a drive (not shown) are assigned to the spring holder body 923. The spindle guide 974 is pivotally journalled on the holder 904. The drive of the spindle guide 974 permits the spring holder body 923 to be shifted in the direction of the spindle in correspondence to double arrow 945. The spring holder body 924 is connected to a holding block 928 via a rotational joint 927. The holding block 928 can be shifted on the lever element 971 by means of a drive (not shown) in correspondence to the double arrow 977.

Links 981 and 982 are assigned to the second carrier arm 902. The links 981 and 982 conjointly with first carrier arm 901 and a section 983 of the second carrier arm 902 form a parallel link.

A second kidney-shaped curved carrier 934 is rigidly connected to the link 982. A second linear spring arrangement 935 acts on curved carrier 934 by means of a roller unit 993 via a lever element 991 which is journalled on the holder 904 with a rotational joint 992. In the same manner as linear spring arrangement 922, the linear spring arrangement 935 has a first spring holder body 936 and a second spring holder body 937 between which the spring blocks 938 are held. The spring holder body 936 includes a spindle 978 and a spindle guide 979 having a drive (not shown) which is pivotally held on the holder 904 with a rotational joint 939.

In the same manner as the spring holder body 923, the spring holder body 936 can be shifted in the direction of the spindle in correspondence to the double arrow 980. In the same manner as the spring holder body 924, the spring holder body 937 is connected to a holding block 969 via a rotational joint 968. The holding block 969 can be shifted in the direction of the spindle in correspondence to double arrow 999. Furthermore, a drive for a movement corresponding to the double arrow 999 on the lever element 991 is assigned to the second spring holder body 937.

The holder 904 is held on a mounting unit 952 in a rotational joint 950 having a rotational axis 951. The mounting unit 952 is mounted to the ceiling 953 of an operating room (not shown in further detail).

The first linear spring arrangement 922 is so adjusted that it compensates a torque caused by the load taken up in the second carrier-arm 902 in the axis of the rotational joint 903 with this load being of the medical-optical equipment unit 908.

The second linear spring arrangement 935 compensates a torque caused in the axis of the rotational joint 905 by the medical-optical equipment unit 908. This torque is transmitted by means of the links 981 and 982 into the axis of the rotational joint 903. For this compensation, the linear spring arrangement 935 acts via a lever element 991 which is journalled on the holder 904 with a rotational joint 992. This lever element 991 acts via the roller unit 993 on the kidney-shaped curved carrier 934.

The linear spring arrangements 922 and 935 are expanded or relaxed in the directions of the double arrows 945 and 946 when there is a shift of the medical-optical equipment unit 908 in the directions indicated by the double arrows 943 and 944. The suitable adjustment of the linear spring arrangements 922 and 935 ensures that, for each possible position of the carrier arms (901, 902) of the surgical microscope ceiling stand 900, the arrangement is held in equilibrium when the roller units 973 and 993 act at the corresponding positions on the kidney-shaped curved carriers (921, 934), respectively. The forms of the kidney-shaped curved carriers 921 and 934 are so selected that the linear spring arrangements 922 and 935 need not be shifted for a force-free movement of the carrier arms (901, 902) of the ceiling stand, that is, for a pregiven load of the medical-optical equipment unit 908, which is carried by the ceiling stand 900, the spindles (978a, 978) of the linear spring arrangements (922, 935) as well as the linear positions of the spring holder bodies (924, 937) need not be shifted on the lever elements (971, 991) for a force-free movement of the arrangement.

In lieu of the linear spring arrangements in the described holding arrangements, spring elements can also be used which exhibit a non-linear relationship between a deforming deflection and a force generated thereby. It is understood that in this case, the form of the corresponding curved carrier on which the spring element acts must be matched also to the functional relationship between force and deflection of the spring element(s).

Basically, the described holding arrangements with weight balance are suitable not only for accommodating medical-optical equipment units or medical instruments but they can generally be used as manipulators for taking up objects, for example, manipulators for work tools in manufacturing facilities of a factory.

It is understood that the foregoing description is that of the preferred embodiments of the invention and that various changes and modifications may be made thereto without departing from the spirit and scope of the invention as defined in the appended claims.

What is claimed is:

1. A holding arrangement including a holding arrangement for a medical-optical instrument, the holding arrangement comprising:
a holder;
a carrier arm for accommodating a load;
said carrier arm having a rotational joint for pivotally supporting said carrier arm therein relative to said holder;
said carrier arm being adapted to accommodate a load thereon which generates a load torque at said rotational joint;
a curved carrier rigidly connected to said carrier arm;
a device for generating a longitudinal force between said holder and said curved carrier and applying said force to said curved carrier for counterbalancing said load torque at said rotational joint;
said device being pivotally connected to said holder;
said carrier arm being pivotally connected to said holder;
said device including a bearing for rolling along on said curved carrier when said carrier arm moves on said holder; and,
said device acting on said bearing with said longitudinal force.

2. The holding arrangement of claim 1, wherein said device includes at least one spring element for generating said longitudinal force.

3. The holding arrangement of claim 2, wherein said spring element is a spring configured as a linear spring.

4. The holding arrangement of claim 1, wherein said rotational joint is a first rotational joint defining a first rotational axis; and, wherein said holding arrangement further comprises a second rotational joint defining a second rotational axis different from said first rotational axis and for permitting a rotation of said carrier arm about said second rotational axis.

5. The holding arrangement of claim 4, further comprising a stand console; a base unit for accommodating said holder; and, said second rotational joint connecting said base unit to said stand console.

6. The holding arrangement of claim 1, wherein said rotational joint is a first rotational joint; and, wherein said holding arrangement further comprises a front link and a second rotational joint connecting said front link to the forward end of said carrier arm; and, said front link is adapted to hold said load.

7. The holding arrangement of claim 6, further comprising means for establishing an operative connection between said front link and said holder to ensure a constant alignment of said front link independently of the position of said carrier arm.

8. The holding arrangement of claim 7, wherein said means for establishing said operative connection includes a tackle assembly or parallel configuration.

9. The holding arrangement of claim 1, wherein said carrier arm has a receptacle for an additional weight.

10. The holding arrangement of claim 9, wherein said additional weight can be displaced on said carrier arm in order to change said load torque occurring in said rotational joint.

11. The holding arrangement of claim 1, wherein said holding arrangement is configured to be a surgical microscope floor stand or a surgical microscope ceiling stand or a surgical microscope wall stand.

12. The holding arrangement of claim 1, wherein said longitudinal force is applied to said curved carrier perpendicularly on the surface thereof.

13. A holding arrangement including a holding arrangement for a medical-optical instrument, the holding arrangement comprising:
a holder;
a carrier arm for accommodating a load;
said carrier arm having a rotational joint for pivotally supporting said carrier arm therein relative to said holder;

said carrier arm being adapted to accommodate a load thereon which generates a load torque at said rotational joint;

a curved carrier rigidly connected to said carrier arm;

a device for generating a longitudinal force between said holder and said curved carrier and applying said force to said curved carrier for counterbalancing said load torque at said rotational joint;

said device being pivotally connected to said holder; and, a base unit having a longitudinal guide arranged thereon for accommodating said holder therein.

14. The holding arrangement of claim 13, wherein said carrier arm is pivotally connected to said holder.

15. The holding arrangement of claim 14, wherein said device includes at least one spring element for generating said longitudinal force.

16. The holding arrangement of claim 15, wherein said spring element is a spring configured as a linear spring.

17. The holding arrangement of claim 13, wherein said rotational joint is a first rotational joint defining a first rotational axis; and, wherein said holding arrangement further comprises a second rotational joint defining a second rotational axis different from said first rotational axis and for permitting a rotation of said carrier arm about said second rotational axis.

18. The holding arrangement of claim 17, further comprising a stand console; a base unit for accommodating said holder; and, said second rotational joint connecting said base unit to said stand console.

19. The holding arrangement of claim 13, wherein said rotational joint is a first rotational joint; and, wherein said holding arrangement further comprises a front link and a second rotational joint connecting said front link to the forward end of said carrier arm; and, said front link is adapted to hold said load.

20. The holding arrangement of claim 19, further comprising means for establishing an operative connection between said front link and said holder to ensure a constant alignment of said front link independently of the position of said carrier arm.

21. The holding arrangement of claim 20, wherein said means for establishing said operative connection includes a tackle assembly or parallel configuration.

22. The holding arrangement of claim 13, wherein said carrier arm has a receptacle for an additional weight.

23. The holding arrangement of claim 22, wherein said additional weight can be displaced on said carrier arm in order to change said load torque occurring in said rotational joint.

24. The holding arrangement of claim 13, wherein said holding arrangement is configured to be a surgical microscope floor stand or a surgical microscope ceiling stand or a surgical microscope wall stand.

25. The holding arrangement of claim 13, wherein said longitudinal force is applied to said curved carrier perpendicularly on the surface thereof.

26. A holding arrangement including a holding arrangement for a medical-optical instrument, the holding arrangement comprising:

a holder;

a carrier arm for accommodating a load;

said carrier arm having a rotational joint for pivotally supporting said carrier arm therein relative to said holder;

said carrier arm being adapted to accommodate a load thereon which generates a load torque at said rotational joint;

a curved carrier rigidly connected to said carrier arm;

a device for generating a longitudinal force between said holder and said curved carrier and applying said force to said curved carrier for counterbalancing said load torque at said rotational joint;

said device being pivotally connected to said holder; and, said curved carrier being configured to have a shape corresponding to a clothes hook.

27. The holding arrangement of claim 26, wherein said carrier arm is pivotally connected to said holder.

28. The holding arrangement of claim 26, wherein said device includes at least one spring element for generating said longitudinal force.

29. The holding arrangement of claim 28, wherein said spring element is a spring configured as a linear spring.

30. The holding arrangement of claim 26, wherein said rotational joint is a first rotational joint defining a first rotational axis; and, wherein said holding arrangement further comprises a second rotational joint defining a second rotational axis different from said first rotational axis and for permitting a rotation of said carrier arm about said second rotational axis.

31. The holding arrangement of claim 30, further comprising a stand console; a base unit for accommodating said holder; and, said second rotational joint connecting said base unit to said stand console.

32. The holding arrangement of claim 26, wherein said rotational joint is a first rotational joint; and, wherein said holding arrangement further comprises a front link and a second rotational joint connecting said front link to the forward end of said carrier arm; and, said front link is adapted to hold said load.

33. The holding arrangement of claim 32, further comprising means for establishing an operative connection between said front link and said holder to ensure a constant alignment of said front link independently of the position of said carrier arm.

34. The holding arrangement of claim 33, wherein said means for establishing said operative connection includes a tackle assembly or parallel configuration.

35. The holding arrangement of claim 26, wherein said carrier arm has a receptacle for an additional weight.

36. The holding arrangement of claim 35, wherein said additional weight can be displaced on said carrier arm in order to change said load torque occurring in said rotational joint.

37. The holding arrangement of claim 26, wherein said holding arrangement is configured to be a surgical microscope floor stand or a surgical microscope ceiling stand or a surgical microscope wall stand.

38. The holding arrangement of claim 26, wherein said longitudinal force is applied to said curved carrier perpendicularly on the surface thereof.

\* \* \* \* \*

UNITED STATES PATENT AND TRADEMARK OFFICE
CERTIFICATE OF CORRECTION

PATENT NO. : 8,205,845 B2
APPLICATION NO. : 12/149621
DATED : June 26, 2012
INVENTOR(S) : Hermann Hammer Page 1 of 1

It is certified that error appears in the above-identified patent and that said Letters Patent is hereby corrected as shown below:

In Column 5:

Line 43: delete " $gML \cos \phi = |\vec{F}_{spring} \times \vec{r} = k\{x-c\}r \sin \psi;$ torque bal-"

and substitute

-- $gML \cos \phi = |\vec{F}_{spring} \times \vec{r}| = k\{x-c\}r \sin \psi;$ torque bal- -- therefor.

Signed and Sealed this
Twenty-eighth Day of August, 2012

David J. Kappos
*Director of the United States Patent and Trademark Office*